United States Patent [19]

Brunner et al.

[11] Patent Number: 5,681,298

[45] Date of Patent: *Oct. 28, 1997

[54] TOILET TRAINING AID CREATING A TEMPERATURE CHANGE

[75] Inventors: Michael Scott Brunner; Debra Hartley Durrance, both of Appleton, Wis.

[73] Assignee: Kimberly-Clark Worldwide, Inc., Neenah, Wis.

[*] Notice: The term of this patent shall not extend beyond the expiration date of Pat. No. 5,649,914.

[21] Appl. No.: 362,029

[22] Filed: Dec. 22, 1994

[51] Int. Cl.$^6$ ............... A61F 13/15; A61F 7/00
[52] U.S. Cl. ............ 604/361; 604/385.1; 602/2; 607/96; 607/108; 607/114
[58] Field of Search ............... 604/291, 385.1, 604/361; 602/2, 41, 42; 607/96, 114, 108

[56] References Cited

U.S. PATENT DOCUMENTS

| | | | |
|---|---|---|---|
| Re. 32,026 | 11/1985 | Yamashita et al. | 126/263 |
| 1,481,208 | 1/1924 | Johnson. | |
| 2,261,473 | 11/1941 | Jennings | 252/379 |
| 2,907,173 | 10/1959 | Robbins | 62/4 |
| 3,175,558 | 3/1965 | Caillouette et al. | 128/403 |
| 3,306,966 | 2/1967 | Matejcek et al. | 264/321 |
| 3,347,237 | 10/1967 | Jones | 128/285 |
| 3,613,687 | 10/1971 | Kennedy | 128/288 |
| 3,661,142 | 5/1972 | Flam | 128/2 H |
| 3,665,920 | 5/1972 | Davis | 128/287 |
| 3,675,654 | 7/1972 | Baker et al. | 128/287 |
| 3,809,096 | 5/1974 | York | 128/403 |
| 3,881,491 | 5/1975 | Whyte | 128/287 |
| 3,976,049 | 8/1976 | Yamashita et al. | 126/263 |
| 3,977,202 | 8/1976 | Forusz et al. | 62/4 |
| 3,980,070 | 9/1976 | Krupa | 126/263 |
| 4,022,211 | 5/1977 | Timmons et al. | 128/287 |
| 4,081,256 | 3/1978 | Donnelly | 62/4 |
| 4,106,001 | 8/1978 | Mahoney | 340/604 |
| 4,295,517 | 10/1981 | Guex et al. | 165/1 |
| 4,340,563 | 7/1982 | Appel et al. | 264/518 |
| 4,405,297 | 9/1983 | Appel et al. | 425/72 S |
| 4,490,147 | 12/1984 | Pierce et al. | 604/378 |
| 4,573,447 | 3/1986 | Thrash et al. | 126/263 |
| 4,615,695 | 10/1986 | Cooper | 604/385 A |
| 4,639,949 | 2/1987 | Ales et al. | 2/400 |

(List continued on next page.)

FOREIGN PATENT DOCUMENTS

| | | |
|---|---|---|
| 0 138 427 | 4/1985 | European Pat. Off. . |
| 0293208B1 | 11/1988 | European Pat. Off. . |
| 0 661 031 | 7/1995 | European Pat. Off. . |
| 0 704 195 | 4/1996 | European Pat. Off. . |
| 3 608 114 | 9/1987 | Germany . |
| 2 244 201 | 11/1991 | United Kingdom . |
| 2244201 | 11/1991 | United Kingdom . |
| 2259018 | 3/1993 | United Kingdom . |
| 2 259 018 | 7/1995 | United Kingdom . |
| WO86/04219 | 7/1986 | WIPO . |
| WO90/08524 | 8/1990 | WIPO . |
| WO93/19716 | 10/1993 | WIPO . |
| WO93/23005 | 11/1993 | WIPO . |
| WO93/25177 | 12/1993 | WIPO . |
| 96/06587 | 3/1996 | WIPO . |

OTHER PUBLICATIONS

Perry's Chemical Engineers' Handbook, Sixth Edition; pp. 3–157 through 3–159; 1984; McGraw–Hill, Inc. United States of America.

R. A. Lofquist et al.; "Hydrophilic Nylon for Improved Apparel Comfort" from the Textile Research Journal, vol. 55, No. 6, pp. 325–333; Jun. 1985.

*Primary Examiner*—John G. Weiss
*Assistant Examiner*—Dennis Ruhl
*Attorney, Agent, or Firm*—Thomas M. Gage

[57] ABSTRACT

An absorbent article such as a training pant includes a moisture barrier, an absorbent assembly, and a temperature change member. The temperature change member includes a temperature change substance that provides a possible total energy change of from about 6 to about 30 cal/cm$^2$ to assist the wearer in recognizing that urination has occurred.

31 Claims, 6 Drawing Sheets

U.S. PATENT DOCUMENTS

| | | | |
|---|---|---|---|
| 4,640,284 | 2/1987 | Ruderian | 128/399 |
| 4,699,823 | 10/1987 | Kellenberger et al. | 428/219 |
| 4,735,622 | 4/1988 | Acuff et al. | 604/361 |
| 4,773,863 | 9/1988 | Douglas, III | 434/247 |
| 4,778,459 | 10/1988 | Fuisz | 604/378 |
| 4,854,332 | 8/1989 | Hanakura et al. | 131/365 |
| 4,865,597 | 9/1989 | Mason, Jr. et al. | 604/385.1 |
| 4,924,084 | 5/1990 | Lask et al. | 250/227.25 |
| 4,938,753 | 7/1990 | Van Gompel et al. | 604/385.2 |
| 4,938,756 | 7/1990 | Salek | 604/368 |
| 4,940,464 | 7/1990 | Van Gompel et al. | 604/396 |
| 4,987,908 | 1/1991 | Sprinkel et al. | 131/365 |
| 5,043,704 | 8/1991 | Blakeney | 340/573 |
| 5,062,839 | 11/1991 | Anderson | 604/385.1 |
| 5,074,854 | 12/1991 | Davis | 604/385.1 |
| 5,123,411 | 6/1992 | Noziri | 128/403 |
| 5,147,343 | 9/1992 | Kellenberger | 604/368 |
| 5,147,345 | 9/1992 | Young et al. | 604/378 |
| 5,167,655 | 12/1992 | McCoy | 604/396 |
| 5,170,781 | 12/1992 | Loomis | 128/118.1 |
| 5,178,139 | 1/1993 | Angelillo et al. | 604/385.1 |
| 5,192,606 | 3/1993 | Proxmire et al. | 428/284 |
| 5,197,958 | 3/1993 | Howell | 604/361 |
| 5,217,447 | 6/1993 | Gagnon | 604/397 |
| 5,266,592 | 11/1993 | Grub et al. | 514/452 |
| 5,277,180 | 1/1994 | Angelillo et al. | 607/114 |
| 5,342,343 | 8/1994 | Kitaoka et al. | 604/385.2 |
| 5,348,750 | 9/1994 | Greenberg | 426/3 |
| 5,520,674 | 5/1996 | Lavon et al. | 604/385.1 |

TOILET TRAINING AID CREATING A TEMPERATURE CHANGE

BACKGROUND OF THE INVENTION

The present invention relates to absorbent articles that facilitate the toilet training process. More particularly, the invention pertains to an absorbent article such as a training pant that provides the wearer with a perceptible temperature change upon urination.

Absorbent articles such as diapers and training pants are useful to absorb and contain body wastes. Such products, and particularly disposable diapers and training pants, have developed to the point where the wearer remains relatively dry and comfortable. For example, current disposable training pants and diapers have the ability to quickly draw and retain liquid away from the wearer's skin.

An initial step in the toilet training process is for a child to recognize when urination is occurring. This may be a substantial hurdle given the proficiency of many absorbent articles in maintaining a dry and comfortable environment. In fact, there may be relatively few external signals to the child that urination is occurring. The ability to recognize when urination occurs may be further hampered because urination may occur during activities which tend to divert the child's attention.

Therefore, what is lacking and needed in the art is an absorbent article that provides the wearer with a distinct indication of when urination occurs.

SUMMARY OF THE INVENTION

In response to the discussed deficiencies in the prior art, a new absorbent article has been developed. Absorbent articles of the present invention provide a temperature change upon contact with an aqueous solution such as urine. As a result, the wearer will notice a distinct, temperature change sensation to assist the wearer in recognizing that urination has occurred.

In one aspect, the present invention concerns an absorbent article including a moisture barrier, an absorbent assembly disposed on the moisture barrier, and a temperature change member disposed with the absorbent assembly. The temperature change member includes a temperature change substance that provides a possible total energy change of from about 6 to about 30 cal/cm$^2$.

In another aspect, the present invention concerns an absorbent article including a moisture barrier, an absorbent assembly disposed on the moisture barrier, and a temperature change member disposed with the absorbent assembly and including a temperature change substance. The absorbent article provides a surface temperature change when wet of from about 5 to about 25 degrees Fahrenheit.

The temperature change substance either absorbs or releases heat when contacted by urine. An absorption of heat by the temperature change substance will provide the wearer with a cool sensation, while a release of heat by the substance will provide the wearer with a warm sensation. In either case, the absorbent article provides the wearer with a distinct indication of when urination occurs.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposed," "disposed on," "disposed with," "disposed at," "disposed near" and variations thereof are intended to mean that one element can be integral with another element, or that one element can be a separate structure bonded to or placed with or placed near another element.

(c) "fabrics" is used to refer to all of the woven, knitted and nonwoven fibrous webs.

(d) "filament" refers to a member having a high ratio of length to diameter or width. Thus, a filament may be a fiber, a thread, a strand, a yarn or any other member or combination of these members.

(e) "liquid impermeable" when used to describe a layer or laminate means that liquid such as urine will not pass through the layer or laminate under ordinary use conditions in a direction generally perpendicular to the plane of the layer or laminate at the point of liquid contact.

(f) "member" when used in the singular can have the dual meaning of a single element or a plurality of elements.

(g) "nonwoven web" means a web of material which is formed without the aid of a textile weaving or knitting process.

(h) "three dimensional" refers to a garment similar to underwear, shorts or pants in that it has continuous leg and waist openings that are bounded by material of which the garment is made. The garment may or may not have manually tearable seams.

These definitions may be defined with additional language in the remaining portion of the specification.

DETAILED DESCRIPTION OF THE PREFERRED EMBODIMENTS

With reference to FIGS. 1–4, an absorbent article 20 formed according to the invention is shown for purposes of illustration as a three-dimensional, disposable training pant for use by a child. The training pant 20 includes a temperature change member 22 that is positioned and adapted to create a distinct temperature change sensation upon urination. Because the temperature change sensation is noticeable to the child, the child's ability to recognize when urination is occurring will be enhanced. The invention may also be embodied in other types of absorbent articles, such as diapers or adult incontinence products. The training pant 20 will now be described in greater detail.

Figure 1:
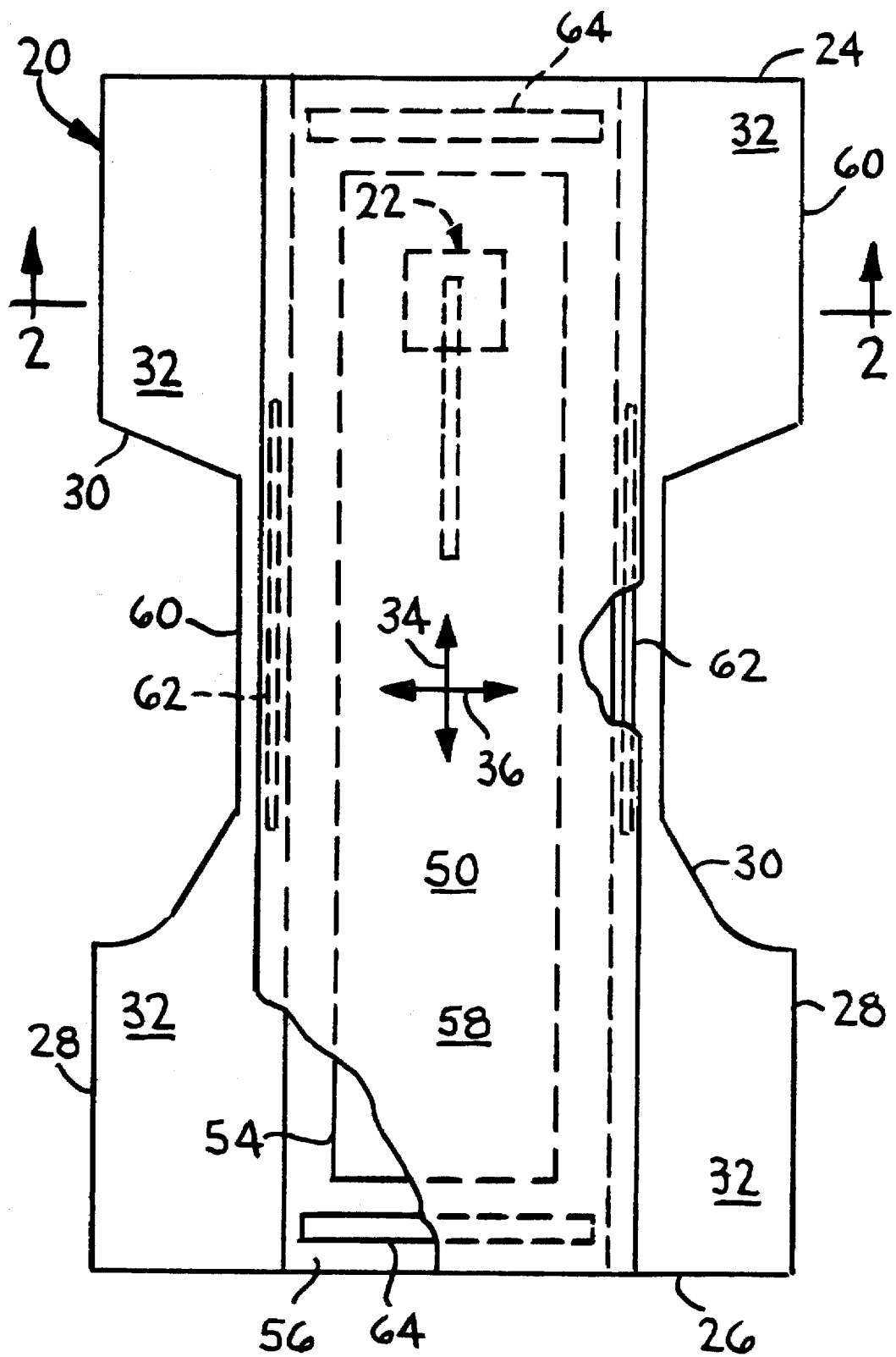
FIG. 1 is a plan view of an absorbent article of the invention, at an intermediate stage of assembly and in a flat and stretched condition, and with portions broken away for purposes of illustration.
Figure 4:
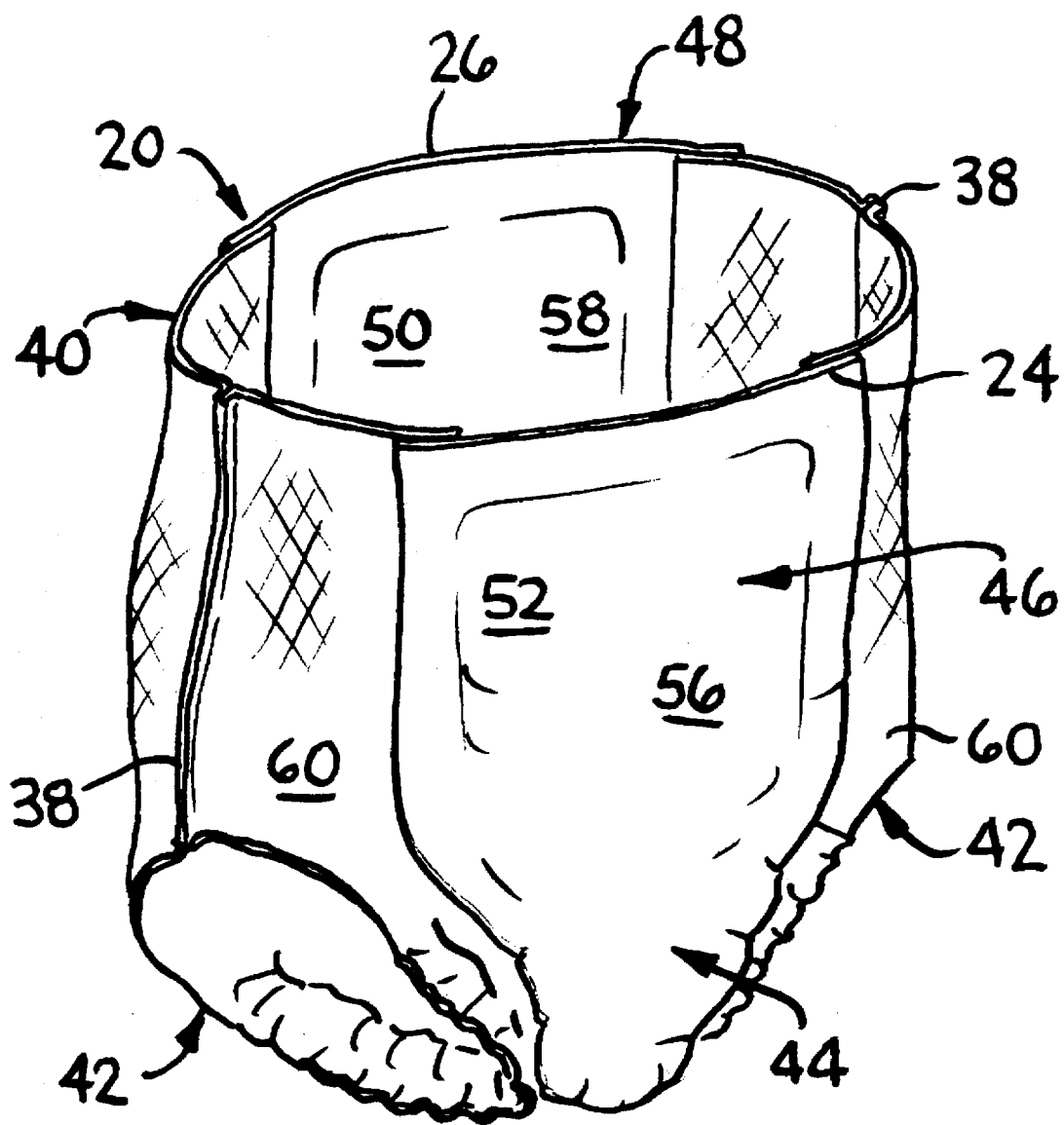
FIG. 4 is a perspective view of the absorbent article of FIG. 1, shown in a fully assembled condition.

The training pant 20 is illustrated at an intermediate stage of assembly and in a flat and stretched condition in FIG. 1 and in a fully assembled form in FIG. 4. The training pant 20 has opposite longitudinally spaced front and back end edges 24 and 26, and opposite side edges 28 extending between the end edges. Each side edge 28 is desirably shaped to form a recessed area 30 with ear portions 32 on either end of the recessed area (FIG. 1). The training pant 20 also defines longitudinal and transverse axes represented by arrows 34 and 36 in FIG. 1.

The training pant 20 is assembled from the intermediate stage shown in FIG. 1 by permanently bonding the ear portions 32 of each side edge 28 together. This is illustrated in FIG. 4 by non-refastenable seams 38. The seams 38, which may be manually tearable, may be formed by any suitable means such as ultrasonic sealing, adhesive bonding, heat sealing, adhesive coated tapes, or the like. One suitable method for forming such seams is disclosed in U.S. Pat. No. 4,938,753 issued Jul. 3, 1990, to Van Gompel et al., which is incorporated herein by reference.

The finished training pant 20 is three-dimensional and thus defines a waist opening 40 and two leg openings 42 (FIG. 4). The finished training pant 20 has a crotch region 44 generally located between the leg openings 42. The crotch region 44 comprises that portion of the pant 20 which, when worn, is positioned between the legs of the wearer and covers the lower torso of the wearer. A front waist region 46 of the training pant 20 extends generally from the crotch region 44 to the front end edge 24, and a back waist region 48 extends from the crotch region to the back end edge 26. In general, the longitudinal extent of the waist regions 46 and 48 is related to the distance between the end edges 24 and 26 of the pant and the recessed areas 30, measured along the side edges 28. The training pant 20 also includes an inner surface 50 and an opposite outer surface 52.

Figure 2:
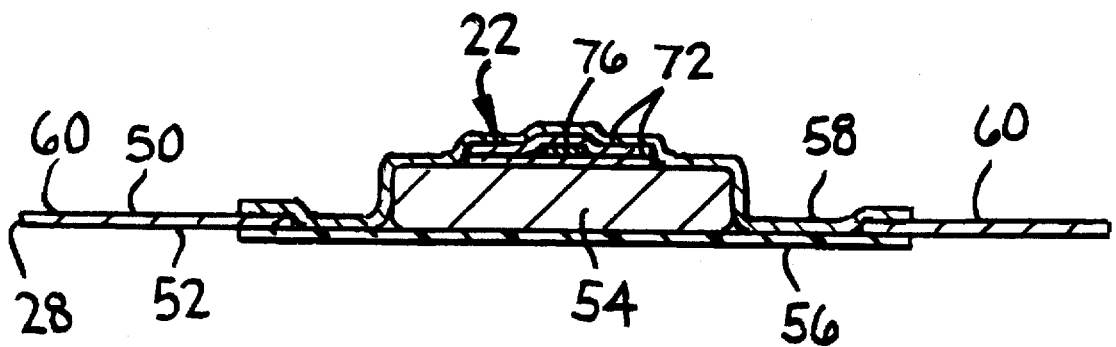
FIG. 2 is a section view taken generally from the plane of the line 2—2 in FIG. 1.

With particular reference to FIGS. 1 and 2, the illustrated training pant 20 comprises an absorbent assembly 54 sandwiched between a moisture barrier 56 and a bodyside liner 58. The moisture barrier 56 and liner 58 are desirably longer and wider than the absorbent assembly 54 and bonded together using adhesives, thermal bonds, ultrasonic bonds or other suitable means. Further, the absorbent assembly 54 is disposed on the moisture barrier 56, and may be bonded directly thereto using adhesives, thermal bonds, ultrasonic bonds or other suitable means. The liner 58 maybe bonded directly to the absorbent assembly 54 as well.

The absorbent assembly 54 may comprise various absorbent materials, such as an air-formed batt of cellulosic fibers (i.e., wood pulp fluff) or a coform material composed of a mixture of cellulosic fibers and synthetic polymer fibers. The absorbent assembly 54 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. and U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 54 may also include tissue layers or acquisition or distribution layers to help maintain the integrity of fibrous absorbents or transport liquids (not shown).

The moisture barrier 56 may, for instance, comprise a single layer of film, a woven material, a nonwoven material or another suitable liquid permeable or liquid impermeable material. The moisture barrier 56 may comprise a thin, substantially liquid impermeable web or sheet of plastic film such as polyethylene, polypropylene, polyvinyl chloride or similar material. Alternatively, the moisture barrier 56 may comprise a nonwoven, fibrous web which has been suitably constructed and arranged to be substantially liquid impermeable. Still alternatively, the moisture barrier 56 may comprise a layered or laminated material, such as a thermally bonded plastic film and nonwoven web composite or a stretch bonded laminate.

The training pant 20 also includes a pair of side panels 60. Each side panel 60 is positioned transversely outward from the absorbent assembly 54 and bonded to the moisture barrier 56, the bodyside liner 58, or both using adhesives, thermal bonds, ultrasonic bonds or other suitable means. The side panels 60 are desirably contoured to form the recessed areas 30 and the ear portions 32 of the pant. Alternately, the training pant 20 could employ four side panels such that each side panel constitutes an individual ear portion 32 of the pant (not shown).

The side panels 60 are desirably formed of an elastic material capable of stretching in a direction parallel to the transverse axis 36 of the training pant 20. Further, the side panels 60 may also be formed of a gas permeable material, referred to as breathable material. The side panels 60 may, for instance, comprise a single layer of apertured film, a woven material, a nonwoven material or another suitable liquid permeable or liquid impermeable material. The side panels 60 may also comprise a laminate material, such as a stretch bonded laminate formed of a prestretched elastic meltblown inner layer sandwiched between and attached to a pair of spunbond polypropylene nonwoven webs having a basis weight of about 13.6 grams per square meter. Suitable elastic materials can be purchased from the Shell Chemical Company of Houston, Tex., under the tradename Kraton.

In one embodiment, the side panels 60 are formed of a laminated material comprising a prestretched elastic meltblown inner layer having a basis weight of about 18 grams per square meter (gsm) sandwiched between and stretch bonded to a pair of spunbond webs each having a basis weight of about 14.9 gsm. The spunbond webs comprise bicomponent fibers formed of about 50 weight percent polypropylene and about 50 weight percent polyethylene in a side-by-side configuration. Alternately, suitable elastic strands may be substituted for the elastic meltblown layer.

The training pant 20 may also include leg elastic members 62 and waist elastic members 64 that are bonded to the moisture barrier 56, the bodyside liner 58, or both to enhance fit and performance (FIG. 1). In particular, the leg elastic members 62 are operatively joined to the moisture barrier 56 along each side edge 28 through the crotch region 44. Also, the waist elastic members 64 are operatively Joined to the moisture barrier 56 along the front and back end edges 24 and 26. The elastic members 62 and 64 may be bonded in place using adhesives, thermal bonds, ultrasonic bonds, stitching, or other suitable means. The elastic members 62 and 64 may be stretch bonded to the moisture barrier 56, bonded in a relaxed state to a gathered portion of the moisture barrier, or a combination of the two. One suitable method for attaching the elastic members 62 and 64 is disclosed in U.S. Pat. No. 4,639,949 issued Feb. 7, 1987, to Ales et al., which is incorporated herein by reference.

Figure 3:
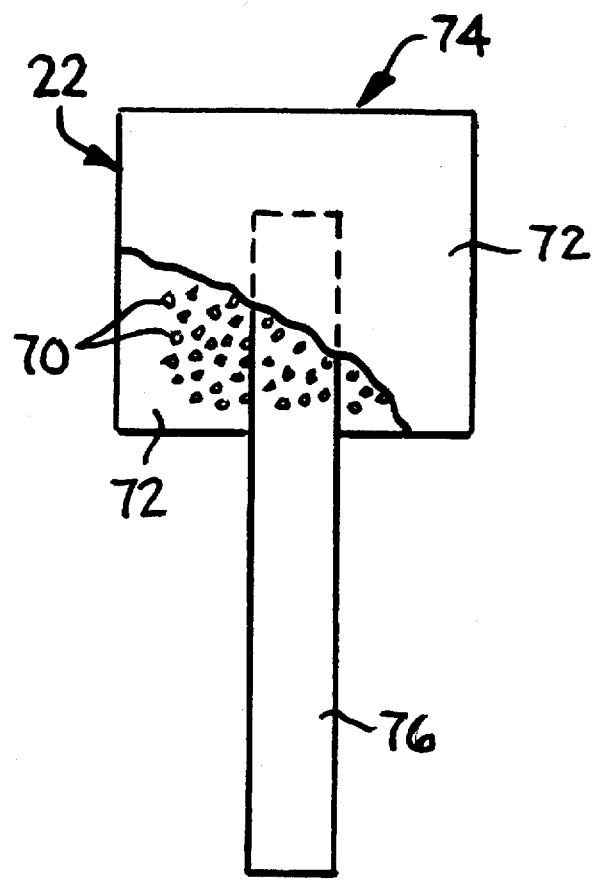
FIG. 3 is a top plan view of a temperature change member of the absorbent article shown in FIG. 1, with portions broken away for purposes of illustration.

As noted previously, the temperature change member 22 is positioned and adapted to create a distinct temperature change sensation upon urination. The temperature change results from a temperature change substance 70 that, in the embodiment of FIGS. 1–3, is in the form of particles captured between a pair of containment layers 72. The containment layers 72 form a container 74 to house and limit movement of the temperature change substance 70. As illustrated, the temperature change member 22 also includes a transport member 76 for transporting liquid into the container 74.

The temperature change substance 70 comprises a material which provides a temperature change when placed near the wearer and contacted with urine. The temperature change can be either an absorption or release of heat to change the temperature of the surroundings to a point noticeable to the wearer. An absorption of heat by the temperature change substance 70 will provide the wearer with a cool sensation, while a release of heat by the substance will provide the wearer with a warm sensation.

The temperature change substance 70 is responsive to contact with an aqueous solution such as urine to either absorb or release heat. The mechanism by which this is accomplished is the dissolution of the substance in the aqueous solution, the swelling of the substance in the aqueous solution, or the reaction of the substance in the aqueous solution. In particular embodiments, the temperature change substance 70 is a particle which has a substantial energy difference between a dissolved state and a crystalline state, so that energy in the form of heat is absorbed or released to the environment upon contact with urine. In other embodiments, the temperature change substance 70 releases or absorbs energy during swelling or reacting of the substance in an aqueous solution.

While a wide variety of substances may result in a temperature change when contacted with an aqueous solution, the selection of a particular temperature change substance 70 and the determination of the amount to be used should be based in part on the desired temperature change. Specifically, the training pant 20 desirably provides a surface temperature change when wet of from about 5 to about 25 degrees Fahrenheit (°F.) (2.8°–13.8° C.). To achieve this result, the temperature change substance 70, the amount used, and the location of the substance should be selected so that the possible total energy change is from about 6 to about 30 calories per square centimeter (cal/cm$^2$), which may represent either a possible total energy release of from about 6 to about 30 cal/cm$^2$ or a possible total energy absorption of from about 6 to about 30 cal/cm$^2$. More desirably, the temperature change substance 70, the amount used, and the location of the substance should be selected so that the possible total energy change is from about 12 to about 24 cal/cm$^2$, and more particularly about 18 cal/cm$^2$.

By way of example, urea particles may be selected to provide a cooling sensation, because urea particles absorb heat when dissolved in an aqueous solution. Urea has a heat of solution of approximately –60 calories per gram (cal/g). A desirable add-on amount for the urea particles would be a basis weight of about 0.3 grams per square centimeter (g/cm$^2$). The selection of urea particles at this basis weight results in a possible total energy change of 60 cal/g×0.3 g/cm$^2$ which equals 18 cal/cm$^2$.

Temperature change substances 70 which absorb or release heat on contact with an aqueous solution desirably have a heat of solution, hydration, or reaction greater than about 40 cal/g or less than about –40 cal/g. The heat of solution, hydration, or reaction is suitably within the range of from about 40 to about 90 cal/g or from about –40 to about –90 cal/g, and more particularly from about 50 to about 70 cal/g or from about –50 to about –70 cal/g, such as urea at –60 cal/g. Suitable basis weights for such temperature change substances 70 range from about 0.1 to about 0.5 g/cm$^2$, and more particularly from about 0.2 to about 0.4 g/cm$^2$.

As referenced above, temperature change substances 70 suitable for use in the training pant 20 include those which dissolve in an aqueous solution. The solubility of such temperature change substances 70 is desirably from about 0.1 to about 3 grams of water (H$_2$O) per gram of material (g/g), and more particularly from about 0.1 to about 2 g/g for improved performance.

Suitable temperature change substances 70 that absorb heat during dissolution can include salt hydrates, such as sodium acetate (H$_2$O), sodium carbonate (10H$_2$O), sodium sulfate (10H$_2$O), sodium thiosulfate (5H$_2$O), and sodium phosphate (10H$_2$O); anhydrous salts, such as ammonium nitrate, potassium nitrate, ammonium chloride, potassium chloride, and sodium nitrate; organic compounds, such as urea, xylitol, and other sugars; or the like. Temperature change substances 70 that release heat during dissolution can include aluminum chloride, aluminum sulfate, potassium aluminum sulfate, or the like. The temperature change substance 70 may also include those substances which absorb or release heat during swelling. By way of illustration, one suitable temperature change particle 70 that releases heat during swelling is a lightly cross-linked partially neutralized polyacrylic acid.

Alternatively, the temperature change substance 70 may include those substances that absorb or release heat upon reaction with an aqueous solution. Examples include ortho esters or ketals such as menthone ketals which result from reacting menthone with alcohols containing 1 to 8 carbons or polyols containing 2 to 8 carbons, and all structural and optical isomers thereof. Particular menthone ketals which may be suitable include menthone-glycerol ketal and menthone-propylene glycol ketal. Particular ketals are disclosed in U.S. Pat. No. 5,348,750 issued Sep. 20, 1994, to Greenberg; and U.S. Pat. No. 5,266,592 issued Nov. 30, 1993, to Grub et al.; which are incorporated herein by reference.

The temperature change substance 70 is desirably although not necessarily in the form of particles sandwiched between the first and second containment layers 72. The first containment layer 72 may, for example, comprise a porous film or fibrous layer. The fibrous layer may comprise a fibrous tissue, a woven or nonwoven fabric, a cellulosic fibrous web, or the like. In one embodiment, for example, the first containment layer 72 can comprise a cellulosic tissue composed of a conventional forming tissue having a basis weight of about 16.6 gsm and manufactured by a continuous wet press (CWP) process from a furnish composed of 100% LL-19 Northern Softwood Kraft (NSWK) fiber. The LL-19 fiber can be obtained from Kimberly-Clark Forest Products, Inc., Terrace Bay, Ontario, Canada. The forming tissue has a Frazier Porosity of about 50–350 cfm/ft$^2$ (cubic-feet-per-minute per square foot).

The second containment layer 72 may, for example, comprise a liquid-permeable web material, such as a liquid-permeable film, tissue, fabric, or the like. The fabric may be woven or nonwoven, and may be composed of a hydrophilic material or composed of a hydrophobic material which has been suitably treated to render it sufficiently hydrophilic. In one embodiment, the second containment layer 72 is composed of a conventional barrier tissue having a basis weight of about 21.2 gsm and manufactured by a CWP machine process from a furnish composed of 50%/50% Hinton EF (Softwood) and LL-16 Northern Hardwood Kraft (NHWK) fiber. The Hinton EF fiber can be obtained from Weldwood, a division of Canada, Ltd., Hinton, Alberta, Canada; and the LL-16 fiber can be obtained from Kimberly-Clark Forest Products, Inc., Terrace Bay, Ontario, Canada. The barrier tissue can have a Frazier Porosity of about 80–120 cfm/ft$^2$.

The temperature change member 22 is positioned within the training pant 20 so that upon urination liquid makes contact with the temperature change particles 70. Thus, the temperature change member 22 is disposed with the absorbent assembly 54 so that urine contacting the absorbent assembly will also contact the temperature change member. Most desirably, the temperature change member 22 is disposed on the bodyside of the absorbent assembly 54 so as to be sandwiched between the absorbent assembly and the bodyside liner 58. In this way, the temperature change resulting from the particles 70 is more easily noticed by the wearer. Alternatively, however, the temperature change member 22 may be located within the absorbent assembly 54 or beneath the absorbent assembly (not shown). The temperature change member 22 may be bonded in position using adhesives, ultrasonic bonds or other suitable means.

The position of the temperature change member 22 may vary off the longitudinal and transverse axes 34 and 36 of the training pant 20. The position and/or structure of the temperature change member 22 should be such that the temperature change particles 70 come in contact with urine during or shortly after urination. The temperature change member 22 is desirably centered in the transverse direction 36. Alternatively, however, the temperature change member 22 may be located off the longitudinal axis 34 of the training pant 20 (not shown).

As illustrated in FIG. 1, the temperature change member 22 may be located so that the temperature change particles 70 are positioned in the front 50 percent of the training pant 20. Because the pant 20 is most likely to be in contact with the wearer in the region of the wearer's abdomen, the temperature change particles are desirably positioned in the front waist region 46 (FIG. 4) and more particularly in the front one third of the length of the training pant 20. Alternatively, the temperature change particles 70 may be positioned in the back waist region 48, such as in the back one third of the length of the training pant 20.

Where the temperature change member 22 is located in the front waist region 46, the transport member 76 is useful to transport liquid deposited in the crotch region 44 to the temperature change particles 70. The transport member 76 has one end positioned in the container 74 in contact with the temperature change particles 70 and an opposite end that is positioned outside the container and desirably extending into the crotch region 44. By way of illustration, the transport member 76 may be rectangular and have a width of about 1 cm (0.4 in) and a length of about 10 cm (4 in).

The transport member 76 is formed of a material and/or treated to transport urine in the plane of the transport member. The transport member 76 may be formed of a web of natural or synthetic fibers. Specific fibers for use in forming such a web include rayon sliver, particularly those having a trilobal geometry, sulfonated pulp, hot calendered pulp or the like.

The temperature change member 22 may be constructed so that urine either enters the container 74 directly through the containment layers 72, is transported into the container by the transport member 76, or both. Where urine is transported into the container 74, for example, the containment layers 72 may comprise a liquid impermeable material, such as a liquid impermeable film, a liquid impermeable nonwoven web, or the like.

The size and shape of the temperature change member 22 may vary widely. For example, an individual temperature change member 22 may be rectangular and measure about 4 cm. (1.6 in) by about 7 cm. (2.8 in). Alternatively, the temperature change member 22 may be in the form of strips (not shown) which extend over the full length or width of the training pant 20. The temperature change particles 70 are desirably localized in regions having a combined area of from about 1 to about 60 cm$^2$, particularly from about 20 to about 40 cm$^2$, such as about 30 cm$^2$ for improved performance. The temperature change member 22 suitably contains from about 1 to about 12 grams, and particularly from about 5 to about 9 grams, for example about 7 grams, of temperature change particles 70.

The bodyside liner 58 may be any soft, flexible, porous sheet which passes liquids therethrough. The liner 58 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The liner 58 has a pore size that readily allows the passage therethrough of liquids, such as urine and other body exudates. The liner 58 maybe selectively embossed or perforated with discrete slits or holes extending therethrough. Optionally, the web or sheet may be treated with a surfactant to aid in liquid transfer. One suitable liner material is a wettable spunbonded polypropylene web produced by the methods and apparatus described in U.S. Pat. Nos. 4,340,563 issued Jul. 20, 1982, and 4,405,297 issued Sep. 23, 1983, to Appel et al., which are incorporated herein by reference.

In particular embodiments, the bodyside liner 58 comprises a wet liner, which is a liner that has a high relative surface moisture upon insult. Use of a wet liner may enhance performance of the temperature change member because the moisture retained may function to conduct heat between the wearer's skin and the temperature change particles 70. The improved conductivity of the wet liner will thus facilitate generation of a cool or warm sensation.

Additionally, the wet liner 58 will provide a wet or damp sensation against the skin upon urination, further drawing the child's attention to the fact that urination has occurred. Wet liners 58 suitable for the present invention desirably cause the training pant 20 to have a relative surface moisture value of at least about 60 percent at approximately 1 minute after a liquid insult, and more particularly at least about 75 percent at approximately 1 minute after a liquid insult for improved performance. A suitable procedure for determining the relative surface moisture value of a training pant 20 is set forth below.

The relative surface moisture in the wet liner 58 and overall training pant 20 is calculated from measurements made using a Surface Dryness Measuring Equipment apparatus manufactured by Hoechst Atkiengesellschaft of West Germany. A detailed description of this type of equipment and its operation can be found in U.S. Pat. No. 4,924,084 issued May 8, 1984, to Lask et al., which is incorporated herein by reference in its entirety. The equipment for this apparatus includes a Strip chart recorder from the Linear Instrument Corporation of Reno, Nev. (Model 1201). The chart recorder records moisture readings from an optical light sensor which in turn is connected to a DC power source. Prior to the conductance of testing, the equipment is turned on and allowed to warm up for a minimum of 45 minutes.

To test a sample, any side panels 60 are removed and any elastics are cut to permit the products to lay as flat as possible. Each sample is placed on top of a plexiglass plate approximately the same size as that of the sample. In order to normalize the moisture values for each sample, a dry reading and a wet reading are both obtained in addition to the actual wetness curve which is generated over a preselected time interval of 10 minutes.

To obtain a dry reading and thus a lower limit on the graph, the sensor is placed over the top of the sample with the longitudinal axis of the sensor being perpendicular to the longitudinal axis of the sample and with the ends of the optical light sensor extending equidistant over both side edges of the sample. The sample is positioned with the liner side adjacent the light sensor and the back sheet facing the plexiglass support. The chart pen is then activated by switching the recorder from stand-by to record and the pen is then zeroed over the 20 grid mark location. The recorder is then returned to stand-by and the detector is removed from the sample.

Next a stainless steel ring having a 6 centimeter inner diameter, a height of 4 centimeters and a weight of approximately 326 grams is centered over the longitudinal and transverse center of the sample in the same location as the dry reading was taken. Into the center of the steel ring there is poured 80 milliliters of certified blood bank saline (Catalogue No. B3158-1) from the Baxter Healthcare Corporation, Scientific Products Division, McGraw Park, Ill. The saline solution is a stabilized isotonic 0.9% saline solution containing no preservatives. The saline solution is at ambient temperature (72° to 74° F.) (22° to 23° C.). The 80 milliliters of saline solution is quickly poured into the ring and thus onto the liner side of the absorbent sample. Immediately after the saline solution is absorbed below the surface of the liner (no excess liquid standing on the liner), the stainless steel ring is removed and the optical light sensor is immediately placed on top of the sample in the same manner as described before and the chart recorder is switched from stand-by to record. The recorder is adjusted to a chart speed of 1 centimeter per minute and the test is allowed to run for a total of 10 minutes.

At the end of the ten minute interval, the chart pen is lifted and the chart it turned off by switching the chart to stand-by. Next, the ring is placed back on top of the sample in the same location as before and the sample is totally saturated by pouring an additional quantity of saline solution generally in an amount of about 100 milliliters so as to completely saturate the absorbent core. The amount of liquid in the pad after the second insult should be enough such that the weight of the sensor causes slight flow back of the liquid to the surface. The ring is then removed and the optical light sensor, whose optical sensing portion is wiped free of any excess saline solution from the previous measurement, is placed in the same location on top of the sample in the same manner as described above. The chart is again switched from stand-by to record and the chart is either momentarily activated or the chart paper is moved back and forth so as to achieve a mark or location on the grid paper representing the total saturation measurement for the sample. Each sample tested then has a zero or dry value ($V_D$), a total saturation value ($V_S$) and a time dependent curve extending from the point of absorption of the initial 80 milliliters of saline solution to a point 10 minutes later.

Following the collection of this data, the relative surface moisture values are calculated using the following equation:

$$\text{relative surface moisture (\%)} = \frac{V_T - V_D}{V_S - V_D} \times 100 = V_R$$

where:

$V_T$ is the value on the curve at a given time.

$V_D$ is the value on the curve when the sample is dry.

$V_S$ is the value on the curve when the sample is saturated.

The wet liner 58 comprises a web of material which is made from a plurality of fibers which can be woven or nonwoven. Suitable webs of material may comprise any type of fiber, such as short staple fibers or longer, more continuous fibers, as are found for example in meltblown and spunbond webs. The fibers may be natural, synthetic or a combination thereof, and may be hydrophilic or hydrophobic by nature or they may be treated to be such. The webs of material may be bonded by methods such as hydroentangling, needling, stitching, heat bonding, adhesive bonding, ultrasonic bonding, through air bonding, point bonding, or the like. Suitable wet liner materials are disclosed in U.S. patent application Ser. No. 08/268,697 of Collier et al. filed Jun. 30, 1994 (Attorney Docket No. 11,521), which is incorporated herein by reference.

One suitable material for the wet liner 58 is a spunbond web having a basis weight of at least about 14 gsm (0.4 osy), The fibers are desirably bicomponent fibers which include a water-absorbing component, such as those formed of a material identified under the tradename HYDROFIL and available from Allied Corporation, Fibers Division of Petersburg, Va., U.S.A. In one embodiment, the fibers are side-by-side bicomponent fibers comprising 40 volume percent HYDROFIL material and 60 volume percent polypropylene. The fiber denier is desirably less than about 2.0 dpf, and more particularly less than about 1.5 dpf for improved performance. The bicomponent spunbond web can be point-bonded or through-air bonded. A spunbond web of this type does not require additional treatments or additives, such as a wettability treatment.

By way of further illustration, the wet liner 58 may also comprise a polypropylene spunbond web with an added absorbent staple fiber component, such as rayon fibers having a staple length of about 2.5 to about 3.2 cm. (1–1.25 inch), fibrous superabsorbent (FSA), or the like. The web suitably has a basis weight of at least about 14 gsm (0.4 osy), and particularly at least about 24 gsm (0.7 osy) for improved incorporation and bonding. The fiber denlet is desirably less than about 2.0 dpf, and more particularly less than about 1.5 dpf for improved performance. The resulting composite could be treated in process with a topically applied surfactant to enhance the rate of wetting.

In an alternative embodiment, the wet liner 58 comprises a bonded carded web containing at least about 20 weight percent rayon staple fibers, such as from about 20 to about 40 weight percent rayon staple fibers. The rayon fibers may have a denlet of at least about 1.5 dpf, and particularly in the range of from about 1.5 dpf to 6 dpf. The bonded carded web desirably has a basis weight of at least about 20 gsm (0.6 osy).

Still alternatively, the wet liner 58 could comprise a-polypropylene or polyethylene meltblown web having a durable wettability treatment. Meltblown fibers are typically in the range of 10–30 microns, but can be made larger ("macrofiber meltblown") if a material having greater permeability is desired. The meltblown web may have a basis weight of at least about 50 gsm, and particularly about 150 gsm.

Other suitable materials include patterned point-bonded coform, for example comprising about 40 weight percent polymer and 60 weight percent pulp. A lower polymer content coform could also be employed in combination with a cover material such as for example, a 14 gsm (0.4 osy) treated spunbond of 3.0 dpf fibers.

Die-cut sheets of hydrophilic foam could also be used for the wet liner 58. Suitable foams include cellulose sponges, polyethylene glycol-based polyurethane foams, polyvinyl alcohol-based foams, or the like. Desirably, the foams are reversibly compressible, meaning that they can be compressed into a stable thin layer and then reconstituted into their original foam structures upon addition of liquid.

In use, the three-dimensional pant 20 is designed to draw the wearer's attention to the fact that urination has occurred. The temperature change member 22 is placed within the pant 20 so that urine enters the container 74 directly through the containment layers 72, is transported into the container by the transport member 76, or both. By either or both methods, urine will come into contact with the temperature change particles 70. Depending on the particular type of particles 70 used in the temperature change member 22, the particles will either absorb or release heat. As a result, the wearer will experience either a cool sensation or a warm sensation upon urination. In instances where the bodyside liner 58 is formed of a wet liner, the wearer may also experience a damp or wet sensation.

The training pant 20 desirably provides a surface temperature change when wet of from about 5 to about 25 degrees Fahrenheit (°F.) (2.8°–13.8° C.). Surface temperature changes within this range are believed to be identifiable to some extent by children of toilet training age. More desirably, the training pant 20 provides a surface temperature change when wet of from about 10° to about 20° F. (5.5°–11.1° C.), and particularly about 15° F. (8.3° C.) for improved performance. Also, the cool or warm sensation produced by the temperature change member 22 should last from about 1 to about 120 seconds, and particularly from about 10 to about 60 seconds, such as about 30 seconds.

A suitable procedure for determining the surface temperature change when wet of a product containing a temperature change substance is as follows. The test should be conducted in an environment having a stable temperature of 21 to 22 degrees Celsius (70°–72° F.) and a stable humidity of about 50 percent. The product to be tested is prepared by removing any elastic side panels and cutting all other elastics to permit the product to lay as flat as possible. The product is positioned in a plexiglass cradle to simulate the configuration of the product in actual use. The center of the product is placed in the deepest portion of the cradle.

A liquid dispensing nozzle operatively connected to a liquid dispensing pump is positioned to dispense saline onto the inner surface of the product. The tip of the nozzle should be is located 1 cm away from the inner surface and 10 cm forward of the center of the product, along the product's longitudinal axis. The pump is activated to dispense 90 milliliters (ml) of a stabilized isotonic 0.9% saline at a rate of 15 ml/sec. The saline is certified blood bank saline available from The Baxter Healthcare Corporation, Scientific Products Division, McGraw Park, Ill., and is at a temperature of 37 degrees Celsius (98.6 ° F.).

The surface temperature of the product at the location of the temperature change substance is measured using a standard thermometer or temperature sensing thermistors connected to a digital display or recording device. The surface temperature 30 seconds after the saline is dispensed is recorded as the test temperature. A reference temperature is obtained by performing this test on a portion of the product not including the temperature change substance or on a similar product without the temperature change substance. The surface temperature change when wet for the product is the difference between the test temperature and the reference temperature.

Figure 5:
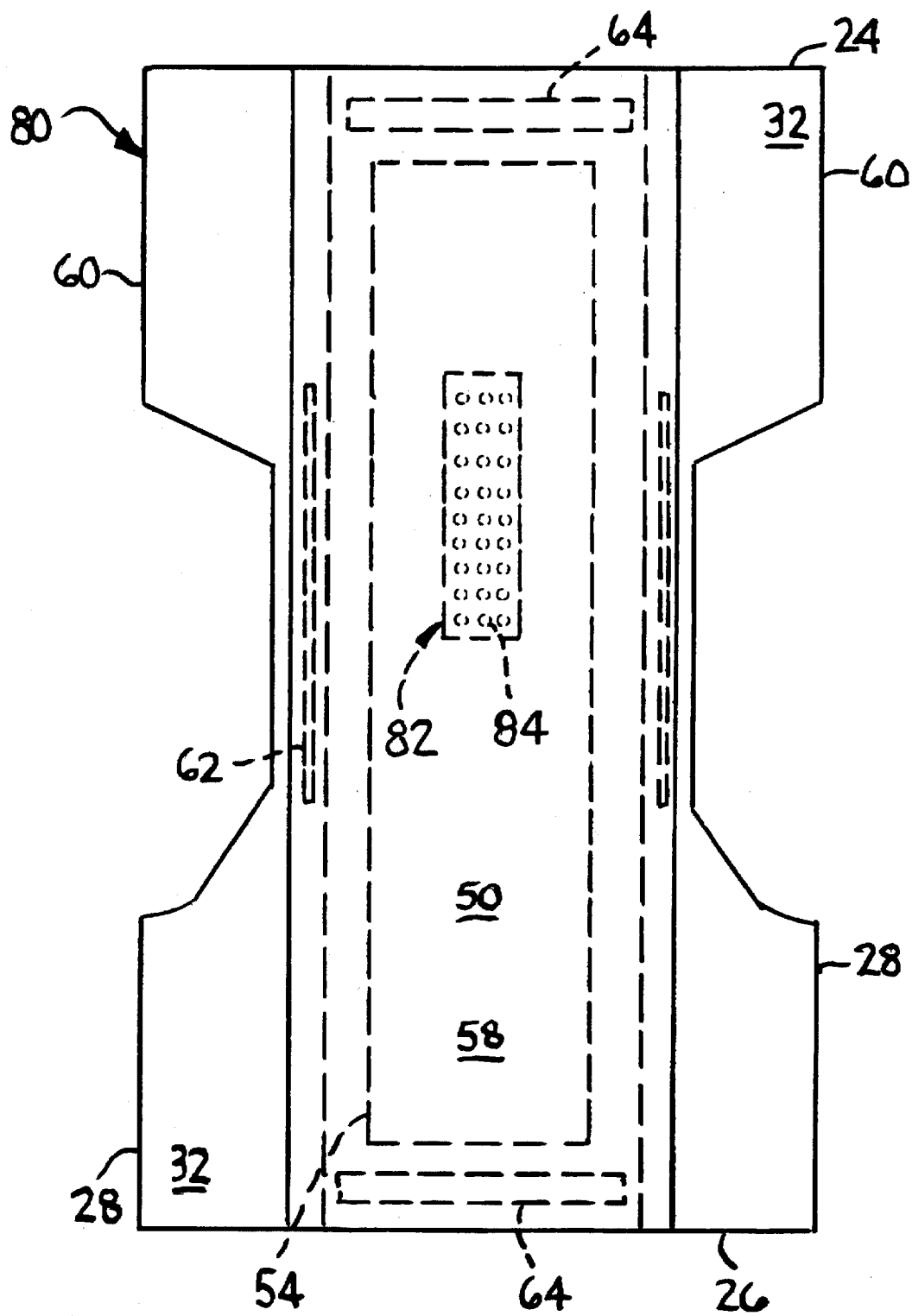
FIG. 5 is a plan view of an alternative absorbent article of the invention, at an intermediate stage of assembly and in a flat and stretched condition.
Figure 6:
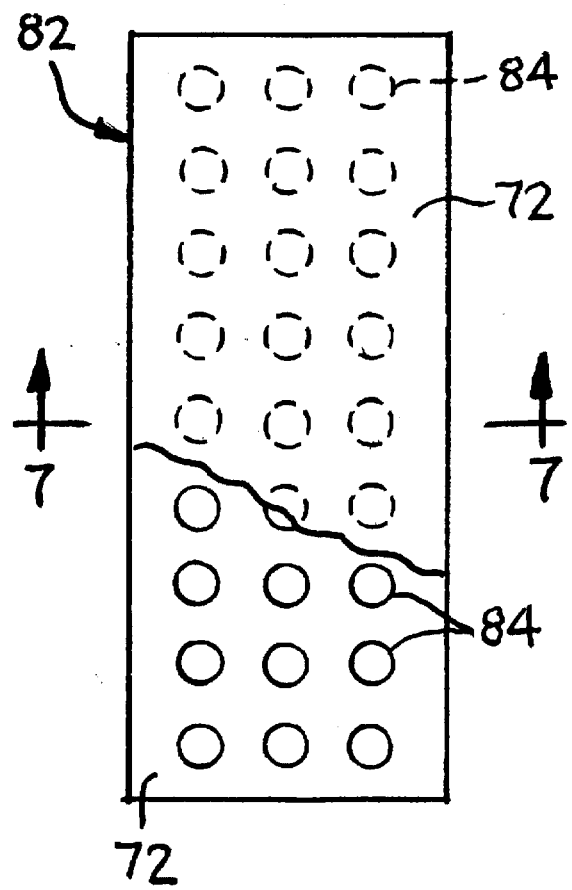
FIG. 6 is a top plan view of a temperature change member of the absorbent article shown in FIG. 5, with portions broken away for purposes of illustration.
Figure 7:
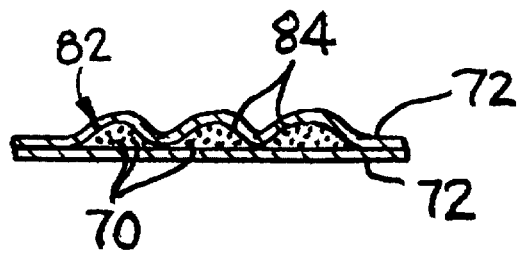
FIG. 7 is a section view taken generally from the plane of the line 7—7 in FIG. 6.

An alternative embodiment of the invention is illustrated by the training pant 80 shown in FIG. 5. Components similar to those previously described have been given the same reference numeral. The training pant 80 of FIG. 5 is similar to the pant 20 of FIG. 1 except for the design and position of a temperature change member 82. FIGS. 6 and 7 illustrate plan and section views of the temperature change member 82.

In this embodiment, the temperature change particles 70 are desirably accumulated in a plurality of pockets 84. Without wishing to be bound by any particular theory, positioning the temperature change particles 70 in discrete pockets 84 is thought to enhance performance because the particles in the interior portions of the pockets are, for an extended period of time, damp rather than saturated. As a result, the heat taken in or released by these temperature change particles 70 as they enter solution, swell or react comes from the surrounding environment rather than solely from the urine. Consequently, locating the temperature change particles 70 in pockets 84 within the temperature change member 82 facilitates generation of a cool or a warm sensation in an efficient and cost effective manner.

The illustrated temperature change member 82 may be constructed by routing the first containment layer 72 onto a forming screen in a forming chamber. The forming screen includes a plurality of spaced apart .holes. A vacuum of 17 KPa (2.5 psi) is drawn on the forming chamber so that the first containment layer 72 is drawn into the holes in the forming screen to define shallow depressions. The temperature change particles 70 are added to form the pockets 84 of temperature change particles. A brush maybe used to evenly distribute the particles 70 into the depressions. A detailed description of an apparatus and process for zoned placement of particulate material is set forth in U.S. patent application Ser. No. 08/274,172 of Heath et al. filed Jul. 12, 1994 (Attorney Docket No. 10,985), which is incorporated herein by reference.

The first and second containment layers 72 may then be secured together by any suitable means such as adhesive bonds, thermal bonds, ultrasonic bonds, stapling, stitching, or the like to sandwich the temperature change particles 70 therebetween. For example, the containment layers 72 may be bonded together by a thin, even or patterned application of construction adhesive applied to the second containment layer 72 before uniting the containment layers 72. The adhesive can be of any suitable type, such as latex adhesive, hotmelt adhesive or the like.

The composite may be pressed together so that any adhesive operably adheres the containment layers 72 together. As a result, the pockets 84 are substantially held and maintained in a desired pattern array composed of individual segregated pockets distributed across the temperature change member 82. The pockets 84 desirably have a diameter of from about 0.5 to 3 cm, and particularly from about 1 to 2 cm, such as about 1.9 cm for improved performance. Additionally, the pockets 84 may be spaced from one another by from about 0.2 to about 10 cm, and particularly from about 0.5 to about 2 cm, such as about 1 cm for improved performance. The basis weight of the temperature change particles 70 within the pockets 84 is suitably from about 0.1 to about 0.5 g/cm$^2$, and more particularly from about 0.2 to about 0.4 g/cm$^2$.

The composite may be pressed together, by way of example, using an assembly roller having a resilient outer cylindrical surface. The assembly roller outer surface can be constructed with a Shore A-Durometer value of not more than about 60, alternatively not more than about 45, or optionally not more than about 30, and with a Durometer value of not less than about 10, alternatively not less than about 15, and optionally not less than about 20. The assembly roller can be urged against the containment layers 72 with a resilient pressuring means, such as a pneumatic actuator. The pressuring means can be constructed to provide an assembly pressure level of not less than about 5 psi, alternatively not less than about 10 psi, or optionally not less than about 15 psi, and constructed to provide an assembly pressure level of not more than about 300 psi, alternatively not more than about 175 psi, and optionally not more than about 50 psi.

Figure 8:
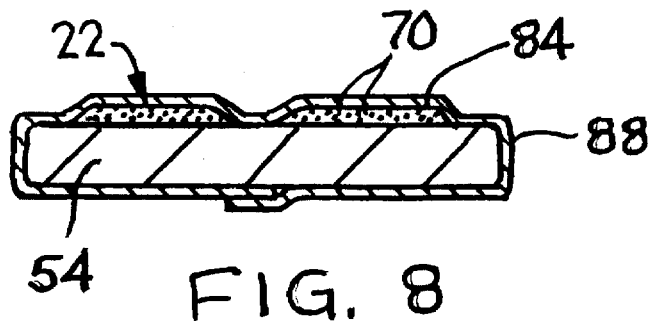
FIG. 8 is a section view of an alternative temperature change member of the present invention.
Figure 9:
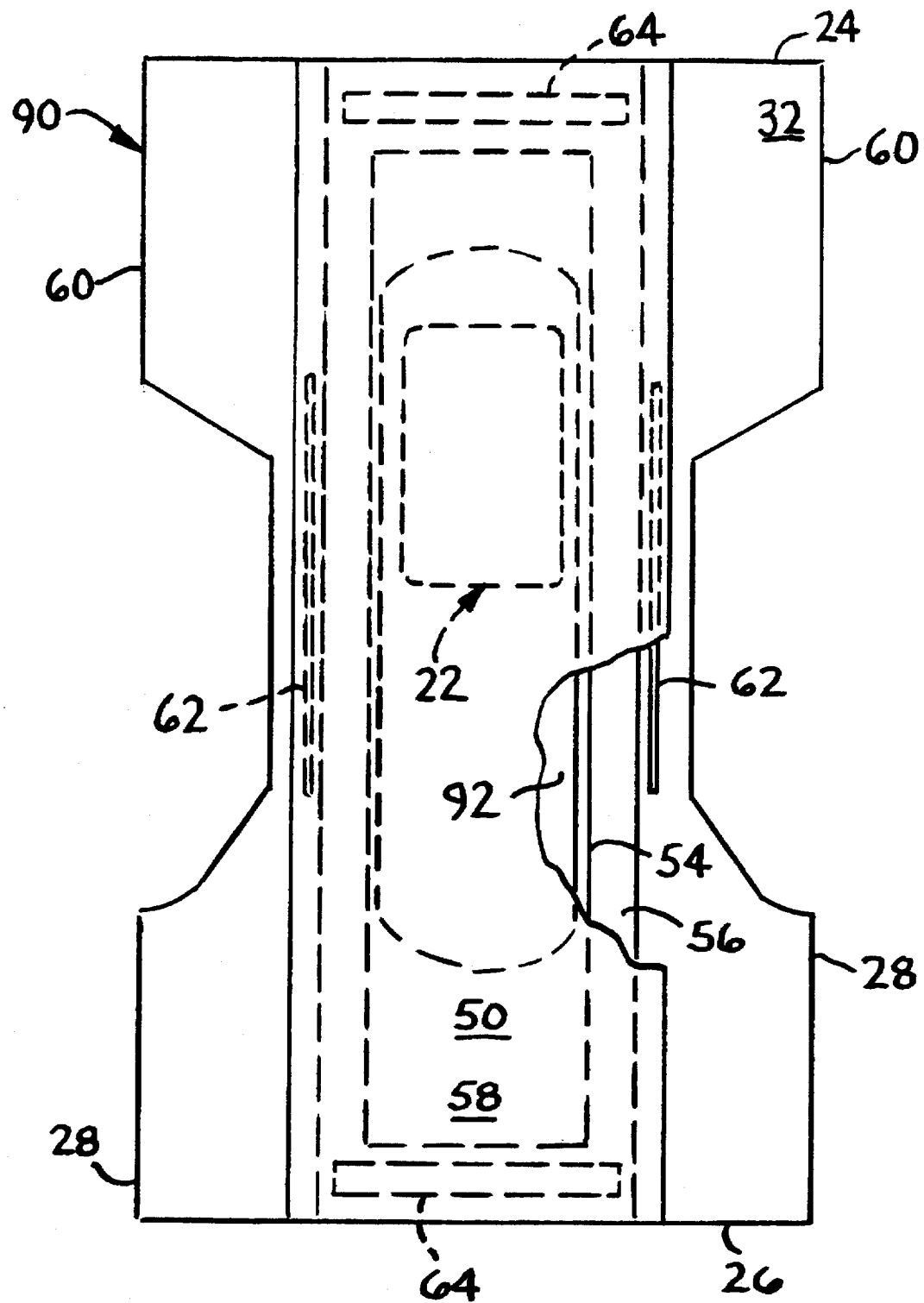
FIG. 9 is a top plan view of another alternative absorbent article of the invention, at an intermediate stage of assembly and in a flat and stretched condition, and with portions broken away for purposes of illustration.

Portions of a further alternative training pant of the invention are illustrated in FIG. 8. The temperature change member 22 in this embodiment comprises the temperature change particles 70 being disposed on the absorbent assembly 54. In particular, the temperature change particles 70 are sandwiched between a wrap sheet 88 and the absorbent assembly 54. The wrap sheet 88 may comprise a nonwoven tissue wrap surrounding the absorbent assembly 54. Alternatively, the wrap sheet 88 may function as the bodyside liner 58 of the pant. The temperature change particles 70 maybe adhesively secured to the wrap sheet 88, the absorbent assembly 54, or both. The particles 70 may be arranged in a thin layer over the surface of the absorbent assembly 54, or localized into pockets 84 of high concentration as shown in FIG. 8. Further, the temperature change member 22 may alternatively comprise a concentration of particles 70 disposed within the absorbent assembly 54 (not shown).

With reference to FIG. 1, an alternative training pant 90 includes a temperature change member 22 that comprises at least a portion of a surge management layer 92. The surge management layer 92 helps to decelerate and diffuse surges of liquid that may be introduced into the training pant 90. In the illustrated embodiment, the surge management layer 92 is located between the bodyside liner 58 and the absorbent assembly 54. Alternatively, the surge management layer 92 may be located on the outer side surface of the bodyside liner 58. The surge management layer 92 may extend over all or only a portion of the absorbent assembly 54, but desirably extends over at least a portion of the crotch region 44 of the pant 90.

Suitable configurations of the surge management layer 92 are described in U.S. Pat. No. 5,192,606 issued Mar. 9, 1993, to D. Proxmire et al.; U.S. patent application Ser. No. 757,760 of W. Hanson et al. filed Sep. 11, 1991 (Attorney docket No. 9922); U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference in a manner that is consistent herewith.

At least a portion of the surge management layer 92 is formed or treated with a temperature change substance 70 (not shown) to form the temperature change member 22. In this instance, the temperature change substance 70 desirably has a high affinity for the fibers of the surge management layer 92, at least prior to contact with urine. The temperature change substance 70 may either absorb or release heat as a result of dissolution or swelling of the substance in the aqueous solution or a reaction including the substance in the aqueous solution.

In one particular embodiment, for example, the temperature change substance 70 comprises a liquid such as a ketal. The temperature change substance 70 may be applied to the fibers of the surge management layer 92 by slot coating, printing, a pulsed spray or another suitable technique.

The foregoing detailed description has been for the purpose of illustration. Thus, a number of modifications and changes may be made without departing from the spirit and scope of the present invention. For instance, alternative or optional features described as part of one embodiment can be used to yield another embodiment. Likewise, the form of the absorbent article may vary greatly. With particular regard to training pants, other suitable structures are described in U.S. Pat. Nos. 4,639,949 issued Feb. 7, 1987, to Ales et al.; 4,938,753 issued Jul. 3, 1990, to Van Gompel et al.; 4,940,464 issued Jul. 10, 1990 to Van Gompel et al.; and U.S. patent application Ser. No. 07/809,993, by Van Gompel et al., filed Dec. 18, 1991, and assigned to the assignee of this application; the disclosures of which are incorporated herein by reference. Additionally, two named components could represent portions of the same structure. Therefore, the invention should not be limited by the specific embodiments described, but only by the claims.

We claim:

1. An absorbent article, comprising:
   a moisture barrier;
   an absorbent assembly disposed on the moisture barrier; and
   a liquid permeable temperature change member disposed with the absorbent assembly and comprising a temperature change substance that is adapted to provide a possible total energy change per unit area of from about 6 to about 30 cal/cm$^2$.

2. The absorbent article of claim 1, wherein the temperature change substance is adapted to provide a possible total energy absorption per unit area of from about 6 to about 30 cal/cm$^2$.

3. The absorbent article of claim 1, wherein the temperature change substance has a substantial energy difference between a dissolved state and a crystalline state.

4. The absorbent article of claim 3, wherein the temperature change substance has a heat of solution within the range of from about 40 to about 90 cal/g or from about −40 to about −90 cal/g.

5. The absorbent article of claim 4, wherein the temperature change substance has a heat of solution within the range of from about 50 to about 70 cal/g or from about −50 to about −70 cal/g.

6. The absorbent article of claim 3, wherein the temperature change substance has a solubility of from about 0.1 to about 3 grams of water per gram of temperature change substance.

7. The absorbent article of claim 1, wherein the temperature change substance is in the form of particles selected from the group consisting of sodium acetate ($H_2O$), sodium carbonate ($10H_2O$), sodium sulfate ($10H_2O$), sodium thiosulfate ($5H_2O$), sodium phosphate ($10H_2O$), ammonium nitrate, potassium nitrate, ammonium chloride, potassium chloride, sodium nitrate, urea, and xylitol.

8. The absorbent article of claim 1, wherein the temperature change substance comprises a ketal.

9. The absorbent article of claim 1, wherein the temperature change substance releases or absorbs energy during swelling in an aqueous solution.

10. The absorbent article of claim 1, wherein the temperature change substance is in the form of particles present at a basis weight of from about 0.1 to about 0.5 $g/cm^2$.

11. The absorbent article of claim 1, wherein the temperature change substance is localized in regions having a combined area of from about 1 to about 60 $cm^2$.

12. The absorbent article of claim 1, wherein the temperature change substance is adapted to provide a possible total energy change per unit area of from about 12 to about 24 $cal/cm^2$.

13. The absorbent article of claim 1, wherein the temperature change substance is in the form of particles located in a plurality of discrete pockets.

14. The absorbent article of claim 13, wherein the pockets have a diameter of from about 0.5 to 3 cm.

15. The absorbent article of claim 14, wherein the pockets have a diameter of from about 1 to 2 cm.

16. The absorbent article of claim 13, wherein the pockets are spaced from one another by from about 0.2 to 10 cm.

17. The absorbent article of claim 16, wherein the pockets are spaced from one another by from about 0.5 to 2 cm.

18. An absorbent article, comprising:
a moisture barrier;
an absorbent assembly disposed on the moisture barrier; and
a liquid permeable temperature change member disposed with the absorbent assembly and comprising a temperature change substance, the absorbent article being adapted to provide a surface temperature change when wet of from about 5 to about 25 degrees Fahrenheit.

19. The absorbent article of claim 18, wherein the absorbent article is adapted to provide a surface temperature change when wet of from about 10 to about 20 degrees Fahrenheit.

20. An absorbent article, comprising:
a moisture barrier;
a bodyside liner bonded to the moisture barrier;
an absorbent assembly sandwiched between the moisture barrier and the bodyside liner; and
a liquid permeable temperature change member disposed with the absorbent assembly and comprising a temperature change substance that is adapted to provide a possible total energy change per unit area of from about 6 to about 30 $cal/cm^2$, the absorbent article being adapted to provide a surface temperature change when wet of from about 5 to about 25 degrees Fahrenheit.

21. The absorbent article of claim 20, wherein the temperature change substance is in the form of particles captured between a pair of containment layers and distributed in a plurality of discrete pockets.

22. The absorbent article of claim 21, wherein the containment layers comprise a liquid-permeable nonwoven web.

23. The absorbent article of claim 20, wherein the temperature change member is sandwiched between the absorbent assembly and the bodyside liner.

24. The absorbent article of claim 20, wherein the absorbent article includes a front waist region, a back waist region, and a crotch region between the front and back waist regions, and the temperature change substance is positioned in the front waist region.

25. The absorbent article of claim 20, further comprising:
a container for housing the temperature change substance; and
a transport member having one end positioned in the container and an opposite end outside the container.

26. The absorbent article of claim 25, wherein the absorbent article includes a front waist region, a back waist region, and a crotch region between the front and back waist regions, and the opposite end of the transport member is positioned in the crotch region.

27. The absorbent article of claim 20, wherein the bodyside liner comprises a wet liner and the absorbent article has a relative surface moisture value of at least about 60 percent at approximately 1 minute after a liquid insult.

28. The absorbent article of claim 20, wherein the temperature change substance is in the form of particles that are adhesively bonded to a nonwoven layer.

29. The absorbent article of claim 20, further comprising a surge management layer disposed on the absorbent assembly, at least a portion of the surge management layer having the temperature change substance applied thereto.

30. The absorbent article of claim 20, wherein the temperature change substance comprises a ketal.

31. The absorbent article of claim 20, wherein the temperature change substance is adapted to provide a possible total energy absorption per unit area of from about 6 to about 30 $cal/cm^2$.

* * * * *